United States Patent [19]

Steinberg et al.

[11] Patent Number: 4,797,218

[45] Date of Patent: Jan. 10, 1989

[54] STABILIZER THIIRANE DERIVATIVES CONTAINING HINDERED PHENOL GROUPS

[75] Inventors: David H. Steinberg, New York; Frank Cortolano, Valhalla, both of N.Y.

[73] Assignee: Ciba-Geigy Corporation, Ardsley, N.Y.

[21] Appl. No.: 898,815

[22] Filed: Aug. 18, 1986

Related U.S. Application Data

[60] Continuation of Ser. No. 836,361, Mar. 5, 1986, abandoned, which is a division of Ser. No. 773,723, Sep. 9, 1985, Pat. No. 4,617,404.

[51] Int. Cl.$^4$ .................. C10M 105/08; C09K 15/08; C09K 15/10; C07D 327/02
[52] U.S. Cl. ..................... 252/47.5; 549/90; 208/18; 208/19; 252/48.6; 252/404; 252/406
[58] Field of Search ...................... 549/90; 208/18, 19; 252/48.6, 404, 406, 47.5

[56] References Cited

U.S. PATENT DOCUMENTS 3,992,420 11/1976 Lind et al. .............................. 549/90

Primary Examiner—Alan L. Rotman
Assistant Examiner—Robert C. Whittenbaugh
Attorney, Agent, or Firm—Harry Falber

[57] ABSTRACT

Compounds of the formula I

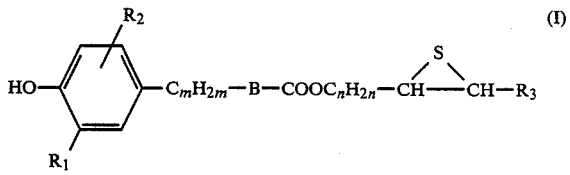

in which $R_1$ and $R_2$, independently, denote alkyl with 1 to 6 carbon atoms, cycloalkyl with 5 to 8 carbon atoms, allyl, methallyl, aralkyl with 5 to 9 carbon atoms, phenyl, 1- or 2-naphthyl, or alkaryl with 7 to 9 carbon atoms, $R_2$ moreover also denotes hydrogen, $R_3$ denotes hydrogen, alkyl with 1 to 6 carbon atoms, unsubstituted phenyl or phenyl substituted by one or two chlorine atoms and/or one or two methyl groups, B denotes a hetero atom, the group —OC(O)—, —OC(O)—CH$_2$CH$_2$— or a direct bond, m is an integer from 0 to 6, and n is an integer from 1 to 6, are prepared by reaction of a thioglycerol derivative with a carboxylic acid containing the hindered phenol moiety in the presence of an acid and are used as antioxidants and thermal stabilizers for lubricating oils, plastics, resins and other organic substrates.

2 Claims, No Drawings

STABILIZER THIIRANE DERIVATIVES CONTAINING HINDERED PHENOL GROUPS

This application is a continuation of application Ser. No. 836,361, filed Mar.5, 1986, now abandoned, which is a divisional of application Ser. No. 773,723 filed on Sept. 9, 1985, now U.S. Pat. No. 4,617,404.

The present invention relates to a process for preparing thiirane compounds, to the use of such compounds as stabilizers for organic polymers and lubricants, as well as to new thiiranes.

Sterically hindered phenols containing a thiirane moiety are known compounds and are described, for example, in U.S. Pat. No. 3,992,420. These compounds are manufactured by reaction of the corresponding oxirane derivatives with thiourea or an alkali metal thiocyanate in a solvent, the oxirane being prepared from the corresponding olefins by reaction with percarboxylic acids or from alkali phenoxides and epichlorohydrins. These methods involve a two-step process and the use of several intermediates and reagents. Furthermore, the overall yield obtained according to these processes and the purity of the resulting end products are, in many instances, unsatisfactory.

Other thiirane compounds absent the hindered phenol group and processes for the preparation thereof are disclosed in U.S. Pat. Nos. 3,359,298, 3,404,158, Lautenschlaeger et al., J. Org. Chem. 34(12), 3991–8 (1969) and Zh. Org. Khim. 12(3), 562–565 (1976).

The present invention provides a process for the production of thiirane compounds having the formula I

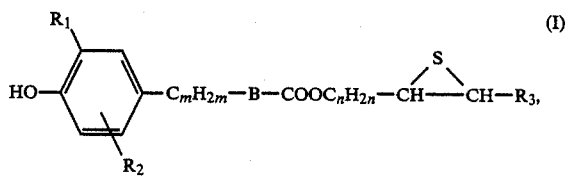

in which $R_1$ and $R_2$, independently, denote alkyl with 1 to 6 carbon atoms, cycloalkyl with 5 to 8 carbon atoms, allyl, methallyl, aralkyl with 5 to 9 carbon atoms, phenyl, 1- or 2-naphthyl or alkaryl with 7 to 9 carbon atoms, $R_2$ moreover also denotes hydrogen, $R_3$ denotes hydrogen, alkyl with 1 to 6 carbon atoms, unsubstituted phenyl or phenyl substituted by one or two chlorine atoms and/or one or two methyl groups, B is a hetero atom, the group $-OC(O)-$, $-OC(O)-CH_2CH_2-$ or a direct bond, m is an integer from 0 to 6, and n is an integer from 1 to 6, which comprises reacting a compound of the formula II

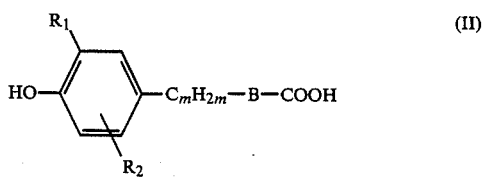

with a thioglycerol of the formula III

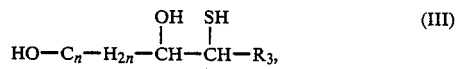

werein $R_1$, $R_2$, $R_3$, B, m and n are defined as above, in the presence of a catalytic amount of an acid, with or without an inert organic solvent.

In the definition of the compounds of formula I, $R_1$, $R_2$ and $R_3$ can be alkyl with 1 to 6 carbon atoms such as, for example, methyl, ethyl, propyl, isopropyl, n-butyl, sec.-butyl, tert.-butyl, amyl, sec.-amyl, tert.-amyl, hexyl or 1,1-dimethylbutyl. Preferably alkyl for $R_1$ is iso-propyl, sec.-butyl, tert.-butyl, iso-amyl and 1,1-dimethylbutyl, and most preferably tert.-butyl. Preferred alkyl for $R_2$ is methyl and tert.-butyl.

$R_1$ and $R_2$ can also be a cycloalkyl group with 5 to 8 carbon atoms such as, for example, cyclopentyl, cyclohexyl, α-methylcyclohexyl or cyclohexyl, or an aralkyl group with 5 to 9 carbon atoms, such as, for example, benzyl α-phenylethyl or α,α-dimethylbenzyl. Preferred are cyclohexyl and benzyl.

$R_1$ and $R_2$ can also be alkaryl with 7 to 9 carbon atoms such as, for example, o-, m- or p-tolyl, 2,3-, 2,4-, 2,5-, 2,6-, 3,4- or 3,5-dimethylphenyl, 2,3,4-, 2,3,5-, 2,3,6-, 2,4,5-, 2,4,6-, 2,5,6- or 3,4,5-trimethylphenyl. Preferred alkaryl for $R_1$ and $R_2$ are o-, m- and p-tolyl.

B can be a hetero atom such as, for example $-O-$, $-S-$ and $-NH-$.

Preferably m is 2 and n is 1.

If $R_3$ denotes phenyl substituted by one or two chlorine atoms and/or methyl groups, it can be, for example, p-chloro- or p-methyl-phenyl and 2-methyl-5-chlorophenyl.

Preferred compounds of formula I are those in which $R_1$ and $R_2$, independently of one another, denote alkyl with 1 to 4 carbon atoms, cycloalkyl or α-methylbenzyl, $R_2$ moreover also denotes hydrogen, $R_3$ is hydrogen or methyl, B is a direct bond, m is the number 2 and n denotes 1.

Particularly preferred compounds of the formula I are those in which $R_1$ is tert.-butyl, $R_2$ is in the ortho position to the hydroxy group and denotes hydrogen, methyl or tert.-butyl, $R_3$ is hydrogen, B is a direct bond, m is 2 and n is 1.

For illustration purposes some specific examples of compounds of formulae II and III are listed. These compounds are generally available as items of commerce or can be manufactured according to known methods of preparation.

Compounds of formula II:
3,5-dimethyl-4-hydroxybenzene-propionic acid
3-methyl-5-tert.-butyl-4-hydroxybenzene-propionic acid
3,5-di-isopropyl-4-hydroxybenzene-propionic acid
3,5-di-tert.-butyl-4-hydroxybenzene-propionic acid
3,5-di-tert.-pentyl-4-hydroxybenzene-propionic acid
3,5-di-tert.-butylbenzylic acid
3,5-di-tert.-butylbenzoic acid
3,5-di-tert.-butylbenzylthioacetic acid
β-(3,5-di-tert-butylbenzylthio)-propionic acid
3,5-di-tert.-butylbenzyloxyacetic acid Compounds of formula III:
1-thioglycerol
3-mercapto-3-methyl-1,2-propan-diol The instant process is carried out by mixing a compound of the formula II and a compound of the formula III in the presence of an acid, without or with an inert organic solvent.

The reaction can be carried out at various temperatures, preferably at a temperature range from 20° C. to 200° C., more preferably from 50° to 150° C. and most preferably from 80° to 110° C. It can be conducted at atmospheric pressure or under pressure.

Inert organic solvents can be, for example, aliphatic or aromatic hydrocarbons such as hexane, heptane, cyclohexane, benzene or benzene substituted by alkyl, alkoxy or halogen, e.g. toluene, xylenes, anisoles, chlorobenzene or dichlorobenzenes, and nitrobenzene; ketones such as cyclohexanone; ethers such a tetrahydrofuran or dioxane; glycol ethers such as ethylene glycol dimethyl or diethyl ether; amides such as dimethylformamide, dimethylacetamide or N-methylpyrrolidone; nitriles such as acetonitrile; and also dimethylsulfoxide or sulfolane. Mixtures of the above-mentioned solvents can also be used. Preferred solvents are toluene, xylene or halogen-substituted benzene.

The process of the present invention is conducted in the presence of an acid. Examples of suitable acids are aliphatic or aromatic carboxylic or sulfonic acids, e.g. formic acid, acetic acid, propionic acid, oxalic acid, benzoic acid, methane sulfonic acid, benzene sulfonic acid or p-toluene sulfonic acid. Further suitable acids include mineral acids such as hydrochloric acid, sulfuric acid or phosphoric acid.

In the process of this invention, the strong acid may be employed in a catalytic amount, preferably 0.001 to 0.20 moles, more preferably 0.02 to 0.10 moles, based on one mole of the compound of the formula II. Compounds of formula II and III are employed in a stoichiometric amount, an excess of the compound of formula III often having an advantageous influence on the yield.

The water formed during the course of the reaction can be removed continuously by azeotropic distillation. The products of the formula I obtained by the process of the invention can be isolated by usual methods such as decantation, extraction, or distillation preferably under diminished pressure. Depending on the envisaged end-use, it may be advantageous to use the crude resulting product or to purify it by distillation or crystallization from an organic solvent.

For the reaction of a compound of formula II with a compound of formula III, one may charge the reaction vessel, at low temperatures, with all the components and then heat the mixture to the desired reaction temperature, or add the individual components to each other within the indicated range of reaction temperatures. A preferred embodiment of the reaction consists in charging the reaction vessel with the compound of the formula II and the acidic catalyst and then adding the compound of the formula III at the desired reaction temperature. A further possibility consists in adding compounds of formulae II and III simultaneously to the acid. It is also possible to carry out the process of the invention batchwise or continuously.

The present invention also relates to new compounds of the formula IV

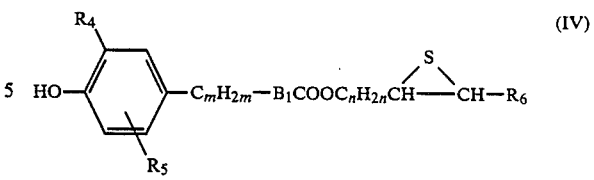

wherein $R_4$ and $R_5$, independently, denote alkyl with 1 to 6 carbon atoms, cycloalkyl with 5 to 8 carbon atoms, allyl, methallyl, aralkyl with 5 to 9 carbon atoms, $R_5$ moreover also denotes hydrogen, m is an integer from 0 to 6, n is an integer from 1 to 6, $B_1$ denotes a hetero atom, the group —OC(O)—, —OC(O)—CH$_2$—CH$_2$— or a direct bond, and $R_6$, when $B_1$ is a direct bond, denotes unsubstituted phenyl or phenyl substituted by one or two chlorine atoms and/or one or two methyl groups, or $R_6$, when $B_1$ is a hetero atom, the group —OC(O)— or the group —OC(O)—CH$_2$—CH$_2$—, denotes hydrogen, alkyl with 1 to 6 carbon atoms, unsubstituted phenyl or phenyl substituted by one or two chlorine atoms and/or one or two methyl groups.

The compounds of the formulae I and IV according to this invention are particularly effective in stabilizing organic materials such as plastics, polymers and resins, mineral and synthetic fluids such as lubricating oils, circulating oils, etc. against oxidative, thermal or actinic degradation.

Substrates in which the compounds of the formulae I and IV according to this invention are particularly useful are polyolefins such as polyethylene and polypropylene; polystyrene, including impact polystyrene, ABS resin, SBR, isoprene, as well as natural rubber, polyesters including polyethylene terephthalate and polybutylene terephthalate, including copolymers, and lubricating oils such as those derived from mineral oil.

In general polymers which can be stabilized include:

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under (1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or α-methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrine homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadien, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadiens with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamid or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymerhomologous manner, such as cellulose acetates, cellulose propionates and cellulose butyrates, or the cellulose ethers, such as methylcellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/butadiene copolymers.

In general, the compounds of the formulae I and IV according to this invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants 1.1. Alkylated monophenols, for example, 2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert.butyl-4-methoxymethylphenol 1.2. Alkylated hydroquinones, for example, 2,6-di-tert.butyl-4-methoxyphenol
2,5-di-tert.butyl-hydroquinone
2,5-di-tert.amyl-hydroquinone
2,6-diphenyl-4-octadecyloxyphenol 1.3. Hydroxylated thiodiphenyl ethers, for example 2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)

1.4. Alkyliden-bisphenols, for example, 2,2'-methylene-bis-(6-tert.butyl-4-methylphenol)
2,2'-methylene-bis-(6-tert.butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-α-methylbenzyl)-4-nonylphenol]
2,2'-methylene-bis-[6-α,α-dimethylbenzyl)-4-nonylphenol]
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl)-butane
2,6-di-(3-tert.butyl-5-methyl-2-hydroxybenzyl)-4-methylphenol
1,1,3-tris-(5-tert.butyl-4-hydroxy-2-methylphenyl)-butane
1,1-bis-(5-tert.butyl-4-hydroxy-2-methylphenyl)3-n-dodecylmercaptobutane
ethyleneglycol-bis-[3,3-bis-(3'-tert.butyl-4'-hydroxyphenyl)-butyrate]
di-(3-tert.butyl-4-hydroxy-5-methylphenyl)-dicyclopentadiene
di-[2-(3'-tert.butyl-2'-hydroxy-5'-methyl-benzyl)-6-tert.butyl-4-methylphenyl]-terephthalate.

1.5. Benzyl compounds, for example, 1,3,5-tri-(3,5-di-tert.butyl-4-hydroxybenzyl)-2,4,6-trimethylbenzene-di-(3,5-di-tert.butyl-4-hydroxybenzyl)sulfide
3,5-di-tert.butyl-4-hydroxybenzyl-mercapto-acetic acid isooctyl ester
bis-(4-tert.butyl-3-hydroxy-2,6-dimethylbenzyl)dithiol-terephthalate
1,3,5-tris-(3,5-di-tert.butyl-4-hydroxybenzyl)-isocyanurate
1,3,5-tris-(4-tert.butyl-3-hydroxy-2,6-dimethylbenzyl)isocyanurate
3,5-di-tert.butyl-4-hydroxybenzyl-phosphoric acid di-octadecyl ester
3,5-di-tert.butyl-4-hydroxybenzyl-phosphoric acid monoethyl ester, calcium-salt 1.6. Acylaminophenols, for example, 4-hydroxy-lauric acid anilide
4-hydroxy-stearic acid anilide
2,4-bis-octylmercapto-6-(3,5-tert.butyl-4-hydroxyanilino)-s-triazine
octyl-N-(3,5-di-tert.butyl-4-hydroxyphenyl)-carbamate 1.7. Esters of β-(3,5-di-tert.butyl-4-hydroxyphenyl)-propionic acid with monohydric or polyhydric alcohols, for example,

| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.8. Ester of β-(5-tert.butyl-4-hydroxy-3-methylphenyl)-propionic acid with monohydric or polyhydric alcohols, for example,

| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.9. Amides of β-(3,5-di-tert.butyl-4-hydroxyphenyl)-propionic acid for example, N,N'-di-(3,5-di-tert.butyl-4-hydroxyphenylpropionyl)-hexamethylendiamine
N,N'-di-(3,5-di-tert.butyl-4-hydroxyphenylpropionyl)-trimethylendiamine
N,N'-di-(3,5-di-tert.butyl-4-hydroxyphenylpropionyl)-hydrazine 2. UV Absorbers and Light Stabilisers 2.1. 2-(2'-Hydroxyphenyl)-benztriazoles, for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl-, 3'-sec.butyl-5'-tert.butyl-, 4'-octoxy, 3',5'-di-tert.amyl-, 3',5'-bis-(α, α-dimethylbenzyl)-derivative.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivative.

2.3. Ester of optionally substituted benzoic acids for example, phenyl salicylate, 4-tert.butyl-phenylsalicilate, octylphenyl salicylate, dibenzoylresorcinol, bis-(4-tert.butylbenzoyl)-resorcinol, benzoylresorcinol, 3,5-di-tert.butyl-4-hydroxybenzoic acid 2,4-di-tert.butyl-phenyl ester and 3,5-di-tert.-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxycinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5-di-tert.butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazol, optionally with additional ligands.

2.6. Sterically hindered amines, for example bis-(2,2,6,6-tetramethylpiperidyl)-sebacate bis-(1,2,2,6,6-pentamethylpiperidyl)-sebacate n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylendiamine and 4-tert.octylamino-2,6-dichloro-1,3,5-s-triazine, tris(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone).

0 2.7. Oxalic acid diamides, for example, 4,4'-dioctyloxyoxanilide, 2,2'-di-octyloxy-5,5'-di-tert.butyl-oxanilide, 2,2'-di-dodecyloxy-5,5'-di-tert.butyl-oxanilide, 2-ethoxy2'-ethyl-oxanilide, N,N'-bis (3-dimethylaminopropyl)oxalamide, 2-ethoxy-5-tert.butyl-2'-ethyloxanilide and its mixture with 2-ethoxy-2'-ethyl-5,4'-di-tert.butyloxanilide and mixtures of ortho- and para-methoxy- as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-.butyl4-hydroxyphenylpropionyl)-hydrazine, 3-salicyloylamino1,2,4-triazole, bis-benzyliden-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaerythrit diphosphite, tris-(2,4-di-tert.butylphenyl) phosphite, di-isodecylpentaerythrityl diphosphite, di-(2,4-di-tert.butylphenyl)pentaerythrityl diphosphite, tristearylsorbite triphosphite, tetrakis-(2,4-di-tert.butylphenyl)-4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythrityl-tetrakis(β-dodecylmercapto)-propionate.

6. Polyamide stabilisers, for example copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticizers, lubricants, emulsifiers, pigments, optical brighteners, flame-proofing agents, anti-static agents, blowing agents and thiosynergists such as dilaurylthiodipropionate or distearylthiodipropionate.

The following examples illustrate the embodiments of this invention. In these examples, all parts given are by weight unless otherwise specified.

EXAMPLE 1

Synthesis of thiaglycidyl 3-(3',5'-di-tert.-butyl4'-hydroxyphenyl)propionate (a) A 500 ml, three-necked reaction flask is charged with 41.76 g (0.15 mole) of 3-(3',5'-di-tert.-butyl-4'-hydroxyphenyl)propionic acid, 1.43 g (0.0075 mole) of p-toluene sulfonic acid and 270 ml of dried toluene. The resulting reaction mixture is stirred and heated to reflux and 17.84 g (0.165 mole) of thioglycerol are added dropwise over a one hour interval while stirring continuously. The water which forms is removed continuously by azeotropic distillation and caught in a Dean-Stark trap. After about 3 1/2 hours reaction at reflux, the starting carboxylic acid is essentially all consumed (TLC evidence). The obtained reaction mixture is cooled to room temperature, transferred to a 1 L. separatory funnel and washed with 100 ml of water. This is repeated with 3×100 ml of water, the final pH being 7.0. The toluene solution of the product is washed with 2×100 ml of saturated brine and dried over molecular sieves for 18 hours. Removal of the sieves by filtration and stripping of the solvent under diminished pressure affords 45.8 g of yellow syrup (87% crude yield).

(b) 45.8 g of the crude product is dissolved in 250 ml of hot hexane and the resulting solution is filtered to remove approximately 0.5 g of insoluble product. This hot hexane filtrate is then treated with 5.0 g of Fulment ® 237 Decolorizing Agent for ~30 minutes. The solution is then filtered hot, allowed to cool to room temperature, and stripped under vacuum. The residue (42.25 g) is redissolved in 150 ml of heptane and re-treated with 4.2 g of Fulment ® 237 while stirring and heating for 30 minutes.

The resulting mixture is filtered warm, allowed to cool to room temperature and seeded (with authentic seeds of A18-106). While stirring gently, the product slowly crystallizes without oiling out. Filtration affords 18.9 g of the product of formula

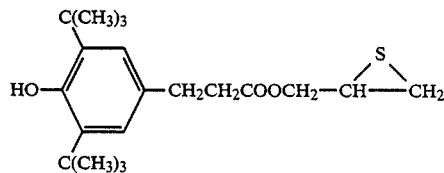

with a melting point of 74°-79° C. and the following microanalysis:

Calculated for $C_{20}H_{30}O_3S$: Found: C%, 68.53; H%, 8.63; S%, 9.15. C%, 68.3; H%, 8.8; S%, 8.9.

EXAMPLE 2

The compound obtained according to Example 1b is evaluated in a lubricating oil as a stabilizer and antioxidant under the following oil oxidation test. This test (standard version according to ASTM 2272, Rotary Bomb Oxidation Test), is carried out in the following manner. An oil sample of 50 g of a 150N Paraffinic mineral oil is oxidized in an oxygen atmosphere, in a glass vessel, together with 5 ml of distilled water and a polished, catalytically active Cu spiral washed with petroleum ether, 0.25% by weight of the stabilizer according to Example 1b being added.

The glass vessel is in a stainless steel bomb with a manometer. The bomb rotates axially at 100 rpm, at an angle of 30° to the horizontal, in an oil bath at 150° C. The oxygen pressure is initially about 6 bars, before heating, increases to exactly 14 bars at 150° C. and remains constant until oxidation has started. The test has ended when there has been a pressure decrease of 1.7 bars. The time is recorded in minutes.

| Stabilizer | Result<br>Minutes until pressure decrease of 1.7 bars |
| --- | --- |
| — | 25 |
| according to Example 1b | 250 |

The increase in time for evidence of the pressure drop is indicative of a good stabilizing effect.

What is claimed is:

1. A composition of matter comprising a lubricating oil subject to oxidative, thermal and actinic degradation stabilized with an effective stabilizing amount of a compound of the formula

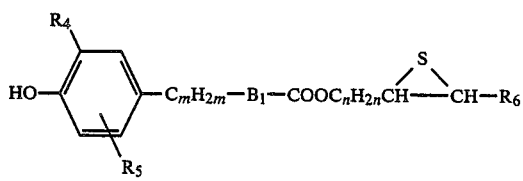

wherein $R_4$ and $R_5$, independently, denote alkyl with 1 to 6 carbon atoms, cycloalkyl with 5 to 8 carbon atoms, allyl, methallyl, aralkyl with 5 to 9 carbon atoms, $R_5$ moreover also denotes hydrogen, m is an integer from 0 to 6, n is an integer from 1 to 6, $B_1$ denotes —O—, —S— or —NH—, the group —OC(O)—, —OC(O)—CH$_2$—CH$_2$— or a direct bond, and $R_6$, when $B_1$ is a direct bond, denotes hydrogen, alkyl with 1 to 6 carbon atoms, unsubstituted phenyl or phenyl substituted by chlorine, methyl or chlorine and methyl.

2. A method for stabilizing a lubricating oil against oxidative, thermal and actinic degradation which comprises incorporating into said lubricating oil an effective stabilizing amount of a compound of the formula

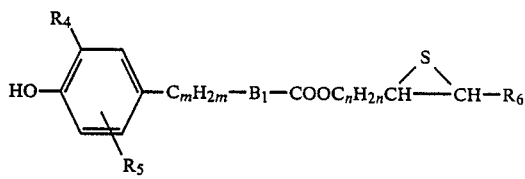

wherein $R_4$ and $R_5$, independently, denote alkyl with 1 to 6 carbon atoms, cycloalkyl with 5 to 8 carbon atoms, allyl, methallyl, aralkyl with 5 to 9 carbon atoms, $R_5$ moreover also denotes hydrogen, m is an integer from 0 to 6, n is an integer from 1 to 6, $B_1$ denote —O—, —S— or —NH—, the group —OC(O)—, —OC(O)—CH$_2$—CH$_2$— or a direct bond, and $R_6$, when $B_1$ is a direct bond, denotes hydrogen, alkyl with 1 to 6 carbon atoms, unsubstituted phenyl or phenyl substituted by chlorine, methyl or chlorine and methyl.

* * * * *